(12) United States Patent
Hommeltoft

(10) Patent No.: US 8,871,154 B2
(45) Date of Patent: Oct. 28, 2014

(54) OLIGOMERIZATION REACTOR AND CONTROL SYSTEM

(75) Inventor: Sven Ivar Hommeltoft, Pleasant Hill, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 198 days.

(21) Appl. No.: 13/586,760

(22) Filed: Aug. 15, 2012

(65) Prior Publication Data

US 2012/0308438 A1 Dec. 6, 2012

Related U.S. Application Data

(60) Division of application No. 12/824,978, filed on Jun. 28, 2010, now Pat. No. 8,471,086, and a continuation of application No. 12/824,854, filed on Jun. 28, 2010, and a continuation of application No. 12/824,893, filed on Jun. 28, 2010, now Pat. No. 8,388,903.

(51) Int. Cl.
*B01J 8/02* (2006.01)
*C07C 2/22* (2006.01)

(52) U.S. Cl.
CPC .............. *C07C 2/22* (2013.01); *C07C 2527/24* (2013.01); *C07C 2527/125* (2013.01)
USPC ........... 422/211; 422/105; 422/110; 422/111; 422/62; 585/527; 585/520; 585/513

(58) Field of Classification Search
None
See application file for complete search history.

(56) References Cited

U.S. PATENT DOCUMENTS

| | | | |
|---|---|---|---|
| 2,407,873 A * | 9/1946 | Evering et al. ............... 585/301 |
| 3,116,346 A | 12/1963 | Ross |
| 4,011,166 A | 3/1977 | Schenach |
| 4,547,612 A | 10/1985 | Tabak |
| 4,990,709 A | 2/1991 | Wu |
| 5,208,403 A | 5/1993 | Buchanan et al. |
| 6,395,948 B1 | 5/2002 | Hope et al. |
| 2004/0035293 A1 | 2/2004 | Davis |
| 2006/0287521 A1 | 12/2006 | Davis |
| 2007/0142691 A1 * | 6/2007 | Elomari et al. ............... 585/727 |
| 2007/0295647 A1 | 12/2007 | Brownscombe et al. |
| 2009/0030229 A1 * | 1/2009 | Riisager et al. ............... 560/129 |
| 2009/0107032 A1 | 4/2009 | Lacheen et al. |
| 2009/0170687 A1 | 7/2009 | Luo et al. |
| 2009/0176956 A1 | 7/2009 | Grinstaff et al. |
| 2009/0306444 A1 | 12/2009 | Elomari et al. |
| 2010/0025292 A1 | 2/2010 | Hommeltoft et al. |
| 2010/0065476 A1 | 3/2010 | Hommeltoft et al. |

FOREIGN PATENT DOCUMENTS

WO 2007124397 11/2001
WO 2005002726 1/2005

OTHER PUBLICATIONS

Hommeltoft, Isobutane alkylation Recent developments and future perspectives, Applied Catalyst A: General 221 (2001) 421-428.
Mehnert, Supported Ionic Liquids Catalysis— A New Concept for Homogeneous Hydroformylation Catalysis, JACS Communications 2002, 124(44), 12932-12933.

* cited by examiner

*Primary Examiner* — Lessanework Seifu
(74) *Attorney, Agent, or Firm* — Susan M. Abernathy

(57) ABSTRACT

A process unit, having:
a) an oligomerization reactor; and
b) a control system that enables the reactor to be operated in a distillate mode and in a lubricant mode; and wherein the reactor can switch between modes.

12 Claims, 1 Drawing Sheet

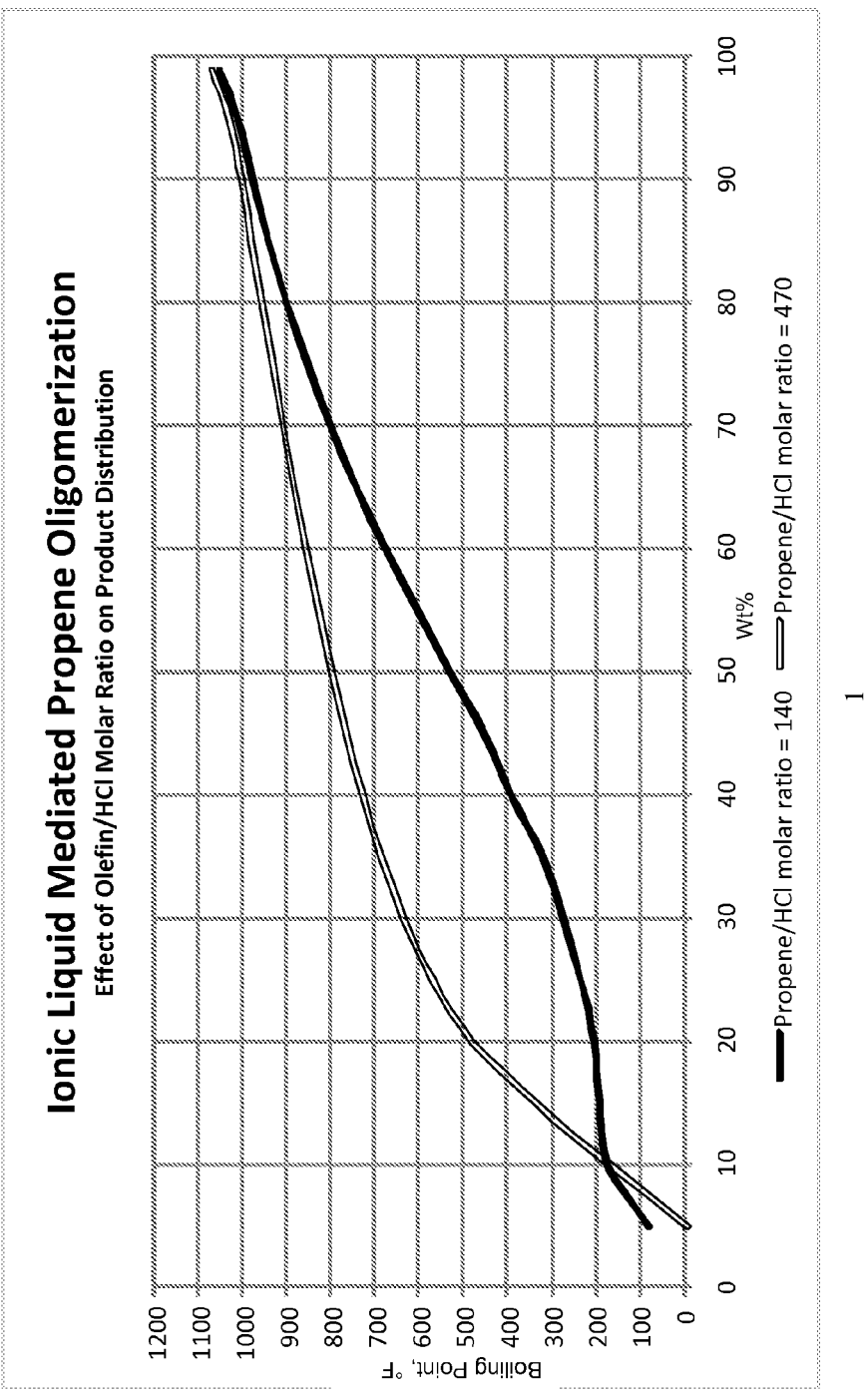

# OLIGOMERIZATION REACTOR AND CONTROL SYSTEM

This application is a division to prior U.S. application Ser. No. 12/824,978, filed on Jun. 28, 2010, and published as US20110319689A1, herein incorporated in its entirety. This application is also a continuation of two co-filed patent applications, US20110319695A1 and US20110318233A1, both filed on Jun. 28, 2010, and herein incorporated in their entireties.

TECHNICAL FIELD

This application is directed to processes for producing distillate and lubricant products, and to a process unit that switches back and forth from producing distillate and lubricant.

SUMMARY

This application provides a process unit, comprising:
a) an oligomerization reactor; and
b) a control system that enables the oligomerization reactor to be operated in a distillate mode wherein greater than 50 wt % of a C5+ product stream boils at 700° F. (371 degree Celsius) or below and in a lubricant mode wherein greater than 50 wt % of the C5+ product stream boils above 700° F. (371 degree Celsius); and wherein the oligomerization reactor can switch back and forth from operating in the distillate mode to the lubricant mode.

BRIEF DESCRIPTION OF THE DRAWINGS

FIG. 1 is a graph showing the effect of different molar ratios of olefin to HCl on product distribution. The line reflecting a propene to HCl molar ratio equal to 470 is the line predominantly above the other line. The other line reflects a propene to HCl molar ratio equal to 140.

DETAILED DESCRIPTION

A 'distillate mode' is a mode of operating the process unit wherein greater than 50 wt % of a C5+ product stream from the process unit boils at 700° F. (371 Celsius) or below. Operation in this mode favors the production of distillate products such as middle distillate and naphtha. A "middle distillate" is a hydrocarbon product having a boiling range between 250° F. to 735° F. (121° C. to 391° C.). The term "middle distillate" includes the diesel, heating oil, jet fuel, and kerosene boiling range fractions. It can also include a portion of naphtha or light oil.

A 'lubricant mode' is a mode of operating the process unit wherein greater than 50 wt % of the C5+ product stream from the process unit boils above 700° F. (371 degree Celsius). Operation in this mode favors the production of lubricants over lighter boiling products. "Lubricants" are hydrocarbons boiling in the range of about 650° F. (343 degree Celsius) and higher. Lubricants can be blended with additives and used for example as diluents for the additives or in finished lubricants. In the context of this disclosure, "distillates" are hydrocarbons boiling in the range less than about 650° F.

The test methods used for boiling range distributions of the product streams in this disclosure are ASTM D 2887-06a and ASTM D 6352-04. The test method is referred to herein as "SIMDIST". The boiling range distribution determination by distillation is simulated by the use of gas chromatography. The boiling range distributions obtained by this test method are essentially equivalent to those obtained by true boiling point (TBP) distillation (see ASTM Test Method D 2892), but are not equivalent to results from low efficiency distillations such as those obtained with ASTM Test Methods D 86 or D 1160.

The adjusting of the molar ratio of olefin to HCl in the process unit can shift the operation of the process unit from operating in different modes. In one embodiment, increasing the molar ratio of olefin to HCl in the process unit provides a higher amount of a lubricant. In another embodiment, decreasing the molar ratio of olefin to HCl in the process unit provides a higher amount of a distillate. In the context of this disclosure "a higher amount" is defined as greater than 50 wt %. In some embodiments the higher amount can be greater than 55 wt %, greater than 60 wt %, greater than 65 wt %, greater than 70 wt %, greater than 75 wt %, greater than 80 wt %, or greater than 85 wt %.

In one embodiment, the molar ratio of olefin to HCl is greater than 130. For example, the molar ratio of olefin to HCL can be greater than 130 in a first mode, greater than 130 in a second mode, or greater than 130 in both modes. In another embodiment, the molar ratio of olefin to HCl is 140 or higher in both modes.

In one embodiment, the molar ratio of olefin to HCl during the distillate mode is lower than during the lubricant mode. The difference in the molar ratios between the distillate mode and the lubricant mode can be 50 or higher, such as from 50 to 1000, from 100 to 800, from 200 to 400, or from 300 to 600. The molar ratio of olefin to HCl is adjusted depending on the configuration of the process unit and the type of catalyst being used.

In one embodiment, the molar ratio of olefin to HCl during the distillate mode is less than 300 or less than 200. For example the molar ratio during the distillate mode can be less than 180, less than 160, or 140 or less. In one embodiment, the molar ratio of olefin to HCl is adjusted to less than 200 to provide the higher amount of the distillate.

In one embodiment, the molar ratio of olefin to HCl during the lubricant mode is higher than during the distillate mode. For example, during the lubricant mode the molar ratio of olefin to HCl can be greater than 200, 250, or 300, such as greater than 400, greater than 450, or from 450 to 1000. In one embodiment, the molar ratio of olefin to HCl is adjusted to greater than 300 to provide the higher amount of the lubricant.

In one embodiment, one or more reactions in the first mode and the second mode comprise oligomerization. Oligomerization is a chemical process that converts monomers to a finite degree of polymerization. Dimers, trimers and tetramers are examples of oligomers formed by oligomerization. In one embodiment the oligomerization is olefin oligomerization. Other reactions that can occur in the first mode and the second mode are olefin alkylation, aromatics alkylation, hydrocracking, dehalogenation, dehydration, hydroisomerization, hydroisomerization dewaxing, and combinations thereof. In one embodiment the one or more reactions in the first mode and the second mode comprise both olefin alkylation and olefin oligomerization.

In one embodiment the operating of the process unit comprises converting hydrocarbons in the presence of a liquid catalyst. The liquid catalyst can be an ionic liquid, another liquid acid, or a combination thereof. The liquid acid can include, but is not limited to, an acid halide (Lewis acid), a metal alkyl, a metal alkoxide, a protic acid (Brønsted acid), or a superacid. For instance, sulfuric acid ("$H_2SO_4$"), hydrofluoric acid ("HF"), phosphoric acid, $AlCl_3$, or $AlBr_3$ can be used as part of or constitute the liquid acid. The liquid catalyst used in the operating of the process unit in the distillate mode can be the same or different from the liquid catalyst used in the operating of the process unit in the lubricant mode.

The ionic liquid is composed of at least two components which form a complex. The ionic liquid comprises a first component and a second component. The first component of the acidic ionic liquid can comprise a Lewis Acid. The Lewis acid can be a metal halide compound selected from components such as Lewis Acidic compounds of Group 13 metals, including aluminum halides, alkyl aluminum halide, gallium halide, and alkyl gallium halide. Other Lewis Acidic compounds, such as Group 3, 4, and 5 metal halides, in addition to those of Group 13 metals, can also be used. Other specific examples include $ZrCl_4$, $HfCl_4$, $NbCl_5$, $TaCl_5$, $ScCl_3$, $YCl_3$, and mixtures thereof. The periodic table by the International Union of Pure and Applied Chemistry (IUPAC), version date 22 Jun. 2007, is used for defining the Groups 3, 4, 5, and 13 metals. In one embodiment the first component is aluminum halide or alkyl aluminum halide. For example, aluminum trichloride can be the first component of the acidic ionic liquid.

The second component making up the ionic liquid catalyst is an organic salt or mixture of salts. These salts can be characterized by the general formula Q+A−, wherein Q+ is an ammonium, phosphonium, boronium, iodonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$, $SO_3CF_3^-$, $CF_3SO_3^-$, $Al_2Cl_7^-$, $AlBr_4^-$, $AlI_4^-$, $AlCl_3Et^-$, $NO_2^-$, $SO_4^-$ and 3-sulfurtrioxyphenyl. In one embodiment the second component is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl substituted pyridinium halide compounds for example 1-butylpyridinium halide, benzylpyridinium halide, or hydrocarbyl substituted imidazolium halides, such as for example, 1-ethyl-3-methyl-imidazolium chloride.

In one embodiment the ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. For example, the ionic liquid catalyst can be an acidic haloaluminate ionic liquid, such as an alkyl substituted pyridinium chloroaluminate or an alkyl substituted imidazolium chloroaluminate of the general formulas A and B, respectively.

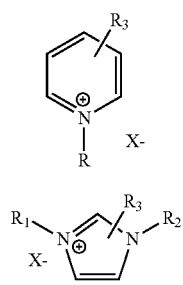

In the formulas A and B; R, $R_1$, $R_2$, and $R_3$ are H, methyl, ethyl, propyl, butyl, pentyl or hexyl group, X is a chloroaluminate. In the formulas A and B, R, $R_1$, $R_2$, and $R_3$ may or may not be the same. In one embodiment the ionic liquid catalyst is N-butylpyridinium chloroaluminate.

In another embodiment the ionic liquid catalyst can have the general formula $RR'R''NH^+Al_2Cl_7^-$, wherein N is a nitrogen containing group, and wherein RR' and R" are alkyl groups containing 1 to 12 carbons, and where RR' and R" may or may not be the same.

The presence of the first component should give the ionic liquid a Lewis acidic character. Generally, the greater the mole ratio of the first component to the second component, the greater is the acidity of the ionic liquid catalyst.

In one embodiment, the process conditions during the first mode and the second mode include a relatively moderate temperature, such that the need for heating and cooling are reduced or eliminated. For example the temperature can be from −20° C. to 100° C. In one embodiment, the temperature is less than 90° C. or less than 50° C. In one embodiment, the temperature is controlled by evaporation of light hydrocarbons in the process unit. In a different embodiment the temperature in the process unit is approximately the same while operating in both the distillate mode and the lubricant mode. In another embodiment, the temperature while operating the process unit in the distillate mode is from 0° C. to 200° C., and the temperature while operating the process unit in the lubricant mode is a higher temperature, from 50° C. to 250° C.

The liquid catalyst can be supported or unsupported. In one embodiment, the liquid catalyst is supported on a fixed bed. The fixed bed can comprise a particulate support material. The particulate support material can comprise a non-basic polar refractory material, such as silica, alumina, titania, zirconia, thoria, boria, niobium oxide, tin oxide, and physical and chemical mixtures thereof. The fixed bed can comprise a porous solid comprising a particulate having a diameter in the longest direction from 25 to 3000 μm. In one embodiment the porous solid or particulate support material is selected from the group consisting of silica, alumina, titania, zirconia, thoria, boria, niobium oxide, tin oxide, and mixtures thereof. In one embodiment, the porous solid has pores in the range of 20 to 150 Å. In another embodiment, the porous solid or particulate support material can comprise polymer resins with pyridine groups, amine groups, other basic groups; or porous forms of carbon, including forms of activated carbon. For example, the porous solid or particulate support material can be protonated forms of polyvinyl pyridine crosslinked with divinyl benzene and/or polystyrene amines.

In one embodiment, the porous solid is able to form an adduct with the liquid catalyst and the porous solid does not react or disintegrate under operating conditions in the process unit under the two modes.

In one embodiment, the particulate support material has a stronger interaction with a fresh ionic liquid than with a passivated ionic liquid. In another embodiment, the fixed bed comprises a particulate support material selected from the group consisting of silica, alumina, titania, zirconia, thoria, boria, and mixtures thereof, and the particulate support material has a stronger interaction with a fresh ionic liquid catalyst than with a passivated ionic liquid catalyst. In these embodiments, a technical advantage is realized because the passivated ionic liquid can be more easily removed from the process unit while retaining the more active ionic liquid in the process unit.

In one embodiment, the liquid catalyst is supported on a fixed bed in a reactor, and sufficient voids remain in the reactor to provide ample flow of the olefin and the HCl. In one embodiment, the HCl is adsorbed onto the liquid catalyst such that the liquid catalyst serves as an adsorbent for the HCl, and the HCl performs a catalytic function. In another embodiment, the liquid catalyst serves as an adsorbent and promoter for the HCl. An adsorbent is a substance, usually porous, that allows the molecules of a gas or liquid to adhere to its large surface area. A promoter is a substance that will accelerate the effect of a catalyst on a reaction.

One technical benefit that can be realized when the liquid catalyst is supported is that some or all of the liquid catalyst remains in the reactor when hydrocarbon products are released from the reactor. This reduces process complexity, as less product clean-up is needed, and there is reduced equipment required for moving the liquid catalyst. Additionally, there can be safety benefits, as when the liquid catalyst remains in the reactor there is less likelihood of exposure of equipment and personnel to toxic or dangerous liquid catalysts.

In one embodiment, a fresh liquid catalyst is added to the process unit and a passivated liquid catalyst is withdrawn from the process unit. The addition and withdrawal of the liquid catalyst can be done continuously or intermittently. The addition and withdrawal of liquid catalyst can be used to maintain a catalyst activity in the process unit. The catalyst activity can be selected from the group consisting of olefin oligomerization, olefin alkylation, aromatics alkylation, hydrocracking, dehalogenation, dehydration, hydroisomerization, hydroisomerization dewaxing, and combinations thereof.

In one embodiment, a hydrocarbon feed stream comprising a mixture of at least one olefin and at least one isoparaffin is fed to the process unit. HCl can be added directly to the feed stream, or supplied separately to the process unit. The at least one olefin can comprise $C_2$ to $C_{14}$ olefins. The at least one isoparaffin can comprise $C_4$ to $C_{12}$ isoparaffins. In one embodiment, the at least one olefin comprises propene and the at least one isoparaffin comprises isobutane.

In addition to adjusting the molar ratio of olefin to HCl in the process unit, the ratio of isoparaffin to olefin can be adjusted. In one embodiment, the difference between the molar ratio of isoparaffin to olefin in the feed stream while operating the process unit in the distillate mode is not substantially different from the molar ratio of isoparaffin to olefin in the feed stream while operating the process unit in the lubricant mode. In this embodiment, this provides for a less complicated process unit design and less fluctuations in flows of the different components of the feed stream. For example the difference can be less than 10, less than 5, less than 2, or less than 1. In one embodiment the molar ratio of isoparaffin to olefin in the feed stream is approximately the same during the distillate mode and the lubricant mode. Approximately the same is defined as a difference from zero to one.

In one embodiment, the process unit comprises an oligomerization reactor and a control system that enables the oligomerization reactor to be operated in the distillate mode and a lubricant mode, and the oligomerization reactor can switch back and forth from operating in the distillate mode to the lubricant mode.

In one embodiment the process unit comprises a catalyst effective for oligomerizing olefins. In one embodiment the catalyst is a liquid catalyst. The liquid catalyst can be an ionic liquid catalyst, as described earlier.

In one embodiment, the control system controls a molar ratio of olefin to HCl. The control system can include flow controllers, for example, to change the molar ratio of olefin to HCl in a hydrocarbon feed stream to the oligomerization reactor. Alternatively, the control system can comprise a recirculation loop for recycling HCl from the effluent from the oligomerization reactor back to the oligomerization reactor.

In one embodiment the oligomerization reactor switches from operating in either the distillate mode or the lubricant mode based on a market demand. For example, there can be seasonal differences in price and demand for middle distillate depending on volumes of shipping and transportation requirements.

In one embodiment the reactor in the process unit can switch back and forth in a short time frame. Examples of short time frames are less than two weeks, less than one week, less than a day, less than 8 hours, less than 5 hours, less than 1 hour, or within half an hour. In one embodiment, the reactor in the process unit can switch back and forth within a few minutes.

EXAMPLES

Example 1

Distillate Mode

A sample of N-butylpyridinium chloroaluminate ($C_5H_5C_4H_9Al_2Cl_7$) ionic liquid catalyst was supported and dispersed in a reactor with a fixed bed of silica gel (4.0 g/9.5 ml DAVISIL™ silica gel, 60 A, 35-60 mesh). DAVISIL® is a registered trademark of W.R. Grace & Co.

A hydrocarbon feed stream comprising a mixture of propene and isobutane was contacted with the ionic liquid catalyst in the reactor. 15 g/hr propene was fed to the reactor. The propene was dissolved in 134 g/hr isobutane, together with 0.09 g/hr HCl. The hydrocarbon feed stream had a propene to HCl molar ratio of about 140. The molar ratio of isoparaffin to olefin was about 6.48.

The reactor was adiabatically operated at 35° C. and 70 psig. The temperature in the reactor was controlled by evaporation of isobutane in the reactor bed. The sample of ionic liquid catalyst was fed to the reactor at a rate of 4-8 g/hr.

The product from the reactor was isolated from the isobutane by distillation. The isolated product was analyzed by SIMDIST. The isolated product was found to contain about 65 wt % boiling in the naphtha-distillate range (BP<700° F.) and 35 wt % boiling in the lubricant range (BP>700° F.). This mode of operation provided a higher amount of distillate, approximately 58 wt %. This is illustrated in FIG. 1 by the lower curve.

Example 2

Lubricant Mode

The same reactor, catalyst, and process conditions described in Example 1 were used. 20 g/hr propene was fed to the reactor. The propene was dissolved in 134 g/hr isobutane, together with 0.037 g/hr HCl. The hydrocarbon feed stream had a propene to HCl molar ratio of about 470. The molar ratio of isoparaffin to olefin was about 4.85.

The product from the reactor was isolated from the isobutane by distillation. The isolated product was analyzed by SIMDIST. The isolated product was found to contain about 35 wt % boiling in the naphtha-distillate range (BP<700° F.) and 65 wt % boiling in the lubricant range (BP>700° F.). This mode of operation provided a higher amount of lubricant, approximately 78 wt %. This is illustrated in FIG. 1 by the upper curve.

The term "comprising" means including the elements or steps that are identified following that term, but any such elements or steps are not exhaustive, and an embodiment can include other elements or steps. For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

What is claimed is:

1. A process unit, comprising:
   a) an oligomerization reactor; and
   b) a control system configured to control a molar ratio of an olefin to a HCl to enable operating the oligomerization reactor;
      i) in a distillate mode wherein greater than 50 wt % of a $C_5^+$ product stream boils at 700° F. (371 degree Celsius) or below, and
      ii) in a lubricant mode wherein greater than 50 wt % of the $C_5^+$ product stream boils above 700° F. (371 degree Celsius); and
   wherein the oligomerization reactor can switch back and forth from operating in the distillate mode to the lubricant mode by controlling the molar ratio.

2. The process unit of claim 1, wherein the oligomerization reactor comprises an ionic liquid catalyst.

3. The process unit of claim 2, wherein the ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof.

4. The process unit of claim 1, wherein the oligomerization reactor switches from operating in either the distillate mode or the lubricant mode based on a market demand.

5. The process unit of claim 1, wherein the oligomerization reactor can switch back and forth in less than a week.

6. The process unit of claim 2, wherein the ionic liquid catalyst is supported on a fixed bed.

7. The process unit of claim 6, wherein the ionic liquid catalyst remains in the oligomerization reactor when hydrocarbon products are released from the oligomerization reactor.

8. The process unit of claim 6, wherein the fixed bed comprises a particulate support material selected from the group consisting of silica, alumina, titania, zirconia, thoria, boria, and mixtures thereof, and wherein the particulate support material has a stronger interaction with a fresh ionic liquid catalyst than with a passivated ionic liquid catalyst.

9. The process unit of claim 6, wherein the ionic liquid catalyst serves as an adsorbent for the HCl.

10. The process unit of claim 6, wherein the ionic liquid catalyst serves as an adsorbent and promoter for the HCl.

11. The process unit of claim 1, wherein the control system comprises a flow controller that changes the molar ratio of the olefin to the HCl in a hydrocarbon feed stream to the oligomerization reactor.

12. The process unit of claim 1, wherein the control system comprises a recirculation loop for recycling an HCl stream from an effluent from the oligomerization reactor back to the oligomerization reactor.

* * * * *